(12) United States Patent
Tournilhac et al.

(10) Patent No.: US 6,238,654 B1
(45) Date of Patent: *May 29, 2001

(54) COSMETIC COMPOSITIONS COMPRISING A FILM-FORMING POLYMER

(75) Inventors: Florence Tournilhac, Paris; Patricia Lemann, Creteil, both of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/348,258

(22) Filed: Jul. 7, 1999

(30) Foreign Application Priority Data

Jul. 7, 1998 (FR) .................................................. 9808687

(51) Int. Cl.⁷ .......................... A61K 7/021; A61K 7/025; A61K 7/42; A61K 7/06; A61K 7/11
(52) U.S. Cl. ................................ 424/63; 424/59; 424/64; 424/70.6; 424/70.7; 424/70.11; 424/401; 514/844; 514/845; 514/938

(58) Field of Search .................. 424/401, 59, 63, 424/64, 70.6, 70.7, 70.11; 514/844, 845, 938

(56) References Cited

U.S. PATENT DOCUMENTS

| | | | |
|---|---|---|---|
| 5,478,562 | * 12/1995 | Cauwet et al. | 424/401 |
| 5,538,717 | * 7/1996 | La Poterie | 424/61 |
| 5,601,808 | * 2/1997 | Mellul et al. | 424/61 |
| 5,650,159 | * 7/1997 | Lion et al. | 424/401 |
| 5,753,215 | * 5/1998 | Mougin et al. | 424/70.11 |

* cited by examiner

Primary Examiner—Shelley A. Dodson
Assistant Examiner—Marina Lamm
(74) Attorney, Agent, or Firm—Oblon, Spivak, McClelland, Maier & Neustadt, P.C.

(57) ABSTRACT

A composition containing a physiologically acceptable medium of oil-in-water or water-in-oil type, thickened by an associative polyurethane. The composition has viscoelastic properties allowing it to recover its initial appearance after each use. The composition may be used as, for example, a makeup foundation.

25 Claims, No Drawings

COSMETIC COMPOSITIONS COMPRISING A FILM-FORMING POLYMER

BACKGROUND OF THE INVENTION

1. Field of the Invention

The present invention relates to an emulsion-type composition of viscous consistency, which may be used for care, treatment or makeup of the skin of both the human face and body, of keratin fibers such as the eyelashes, eyebrows and hair, or even of the lips. The composition may be a makeup foundation, a rouge or eye shadow, a concealer, a lip cream, a mascara or a body makeup product, when prepared in colored form, or else a skin-care cream, an after-shampoo, a shampoo, a sunscreen or skin-tanning cream, or even a dermatological ointment, when it is prepared in colorless form.

2. Description of the Background

Thickened care or makeup compositions generally contain a thickening agent which makes it easy to remove the product from the container without loss of product, permitting the product to be distributed homogeneously over the zone to be treated or sufficient quantities of product to be removed in order to achieve the intended cosmetic effect. In this type of composition, the thickening agent can be hydrophilic or lipophilic. When the composition is sufficiently thick, removal of product with the finger leaves hollow portions on the surface of the product in the container and, at the time of subsequent removal, the product surface has remained unchanged, especially at the time of preceding closing of the jar; the cream then appears to be spoiled, causing dissatisfaction with consumers.

Failure of the cream surface to become level after each use occurs, in particular, for a non-flowing cream of rich and/or thick texture.

A need therefore exists for a composition for makeup, treatment or care of the skin and of keratin fibers which achieves good leveling of the surface in its container, giving the impression of opening a new jar on each occasion and of touching an unspoiled product.

SUMMARY OF THE INVENTION

It is an object of the present invention to provide a composition containing a physiologically acceptable medium, thickened by an associative polyurethane, where the medium contains a liquid fatty phase and an aqueous phase in the form of an emulsion.

It is another object of the invention is the use of the associative polyurethane in a cosmetic composition of the thickened type and the use of associative polyurethane for the manufacture of a dermatological composition of viscous consistency of the emulsion type, especially in oil-in-water form.

It is another object of the present invention to provide a method of treating skin with the composition.

It is another object of the present invention to provide a method of treating keratin fibers with the composition.

It is another object of the invention to provide a method of preparing such a composition.

Accordingly, the objects of the invention, and others, may be accomplished with a composition suitable for topical application to human skin, in the form of an emulsion, and comprising a liquid fatty phase, an aqueous phase, and an associative polyurethane.

By virtue of the associative polyurethane, the composition may have a thick texture, which spreads easily, is rheofluidizable (the viscosity decreases as shear rate increases), and has significant viscoelasticity.

The objects of the invention may also be accomplished with a method of preparing the composition by combining the liquid fatty phase, the aqueous phase, and the associative polyurethane.

The objects of the invention may also be accomplished with a method of treating skin and/or keratin fibers by applying the composition to the skin and/or the fibers.

Various other objects, features and attendant advantages of the present invention will be more fully appreciated as the same becomes better understood from the following detailed description.

DETAILED DESCRIPTION OF THE INVENTION

The associative polyurethanes are nonionic block copolymers containing in the chain both hydrophilic sequences, which most often are of polyoxyethylene nature, and hydrophobic sequences, which may be aliphatic chains alone and/or cycloaliphatic and/or aromatic chains.

In particular, these polymers contain at least two lipophilic hydrocarbon chains of 6 to 30 carbon atoms, separated by a hydrophilic sequence, the hydrocarbon chains being able to be side chains or chains at the end of hydrophilic groups. In particular, it is possible for one or more side chains to be provided. In addition, the polymer may contain a hydrocarbon chain at one or both ends of a hydrophilic sequences.

The polymers can be sequences having three-block or multi-block form. The hydrophobic sequences can therefore be at each end of the chain (for example: three-block copolymer with hydrophilic central sequence) or distributed both at the ends and in the chain (multisequence copolymer, for example), The polymers may also have a grafted or radiating structure.

Preferably the polymers are three-block copolymers whose hydrophilic sequence is a polyoxyethylene chain containing 50 to 1,000 oxyethylene groups. This range includes all specific values and subranges therebetween, such as 75, 100, 200, 300, 500 and 750 oxyethylene groups.

In general, the associative polyurethanes contain a urethane bond between the hydrophilic sequences, hence the origin of the name of this type of polyurethane polymer. By extension, the associative polyurethanes also include polymers whose hydrophilic sequences are connected by other chemical bonds to the lipophilic sequences.

As an example of associative polymers which may be used in the invention, is the polymer $C_{16}$-$OE_{120}$-$C_{16}$ sold by the Huls Co. (under the name Serad FX 1100, a molecule with urethane function and weight-average molecular weight of 1300), OE being an oxyethylene unit. As associative polymer that may also be used is Rheolate 205, with urea function, sold by the Rheox Co., or else Rheolate 208 or 204. These associative polyurethanes are sold in pure form.

The product DW1206B of Rohm & Haas, with a $C_{20}$ alkyl chain and urethane bond, sold as 20% dry material in water, may also be used.

There can also be used solutions or dispersions of these polymers, especially in water or in aqueous alcoholic solution. An example of such polymers is Serad FX1010 and Serad 1035 sold by the Huls Co., and Rheolate 255, Rheolate 278 and Rheolate 244 sold by the Rheox Co. The products DW 1206F and DW 1206J as well as Acrysol RM 184 or Acrysol 44 of Rohm & Haas, may also be used.

The polymers which can be used in the invention are in particular those described by G. Fonnum, J. Bakke and Fk. Hansen, Colloid Polym. Sci. 271, 380–389 (1993), incorporated herein by reference.

The composition of the present invention may contain one or more associative polyurethanes in a quantity sufficient to obtain a thickened rheofluidizing composition with a viscosity of 1,000 to 10,000 cp (or 1 to 10 Pa.s), preferably 2,000 to 6,000 cp (or 2 to 6 Pa.s measured at 25° C. with a moving element turning at 100 rpm and, for example, with a Rheomat 115 viscosimeter. These ranges for the viscosity include all specific values and subranges therebetween, such as 1,500, 2,500, 3,000, 5,000, 7,000 and 9,000 cp. In view of obtaining a stable thickened composition, it is advantageous to use at least 5 mg/$M^2$ and preferably at least 10 mg/$M^2$ of associative polyurethane per unit of developed surface of oil in water.

The composition according to the invention can be one of oily continuous or external phase or of aqueous continuous phase. It can be a simple oil-in-water or water-in-oil emulsion or a triple or multiple emulsion. The composition may be, in particular, in the form of a cream or ointment. Preferably, the continuous phase is an aqueous phase.

The compositions with aqueous continuous or external phase have the advantage of spreading easily, of being light, of penetrating readily into the skin, of being non-sticky and of endowing the skin with freshness during application, in contrast to compositions of oily continuous phase.

According to the invention, the aqueous phase can contain water, an aqueous alcoholic medium and in particular a polyol-containing medium.

In one embodiment, the associative polyurethane or polyurethanes act as emulsifier for the oily phase in the aqueous phase. When the associative polyurethane is used solely as emulsifier, it is very advantageously present in proportions ranging from 2 to 20% by total weight of the composition, preferably in proportions ranging from 3 to 10% by weight. These ranges include all specific values and subranges therebetween, such as 2.5, 4, 5, 8, 10, 12 and 15% by weight.

According to the invention, it is possible to associate with the associative polyurethane one or more surfactants compatible with the oily phase. This surfactant or these surfactants can represent from 0 to 15% and preferably from 0 to 5% of the total weight of the composition. These ranges include all specific values and subranges therebetween, such as 0.01, 0.05, 0.1, 0.2, 0.5, 1, 2, 2.5 and 3% by weight. In a preferred embodiment, the composition does not contain surfactant, which is particularly attractive for persons with sensitive skin. In particular, the composition can be used as a vehicle for an ointment with dermatological properties.

In the presence of surfactant, the associative polyurethane may represent from 0.1 to 20% of the total weight of the composition. This range includes all specific values and subranges therebetween, such as 0.2, 0.5, 1, 2, 5, 8, 10, 12, 15 and 18% by weight.

When the emulsion is of oil-in-water type, the associative polyurethane permits a polymeric "network" to be formed on the skin during application, ensuring in particular spontaneous closing up and leveling of the relief of the skin.

The composition according to the invention can advantageously contain a plurality of coloring materials such as the lipophilic or hydrophilic coloring agents, the pigments, and the nacres. The term "pigment" refers to white or colored particles of inorganic or organic nature, insoluble in the liquid fatty phase, intended to color and/or opacify the composition.

The term "nacres" refers to iridescent particles, especially produced by certain mollusks in their shell or even synthesized. The term "coloring agents" refers generally to organic compounds soluble in fatty substances such as oils or in an aqueous alcoholic phase.

The coloring materials may represent from 0.01 to 60% of the total weight of the composition, preferably from 0.05 to 35% and more particularly from 1 to 20%. These ranges include all specific values and subranges therebetween, such as 0.02, 0.1, 2, 5, 10, 15, 25, 35 and 55% by weight.

Examples of inorganic pigments which can be used in the invention include the oxides of titanium, zirconium or cerium as well as the oxides of zinc, iron or chromium, and Prussian Blue and mixtures thereof. Among the organic pigments which can be used in the invention there can be cited carbon black and the barium, strontium calcium and aluminum lakes, as well as mixtures thereof.

The liposoluble coloring agents which can be used in the invention are, for example, Sudan Red, DC Red 17, DC Green 6, β-carotene, soy oil, Sudan Brown, DC Yellow 11, DC Violet 2, DC Orange 5, Quinoline Yellow and mixtures thereof. They can represent from 0.01 to 20% and preferably from 0.1 to 10% of the total weight of the second composition. The usable water-soluble coloring agents are in particular copper and iron sulfate, water-soluble sulfopolyesters such as those described in FR-96 154152, incorporated herein by reference, the rhodamines, the natural coloring agents (carotene, beet juice), Methylene Blue and mixtures thereof.

The nacres can be present in the composition of the invention in a proportion of 0 to 20% of the total weight of the composition, preferably in a proportion on the order of 1 to 15%. These ranges includes all specific values and subranges therebetween, such as 0.1, 0.5, 2, 10, and 12% by weight. Among the nacres which can be used in the composition there can be cited mica covered with titanium oxide, iron oxide, natural pigment or bismuth oxychloride, such as colored titanium mica, and mixtures thereof.

The composition according to the invention comprises an oily phase, or, in other words, a fatty phase liquid at ambient temperature (25° C.), containing one or more oily liquids which are mutually compatible. The oils according to the invention are not surfactants and advantageously have an IOB value (Inorganic/Organic Balance) of less than 0.42. The IOB parameter is known to a person skilled in the art from a number of publications, such as A. Fujita, Pharm Bull. 2, 163–173 (1954), J09/151109, J08/217639 of Shiseido, or J09/175925 of Kosé. Each of the publications is incorporated herein by reference.

Examples of oils which may be used in the composition of the invention include:

the hydrocarbon oils of animal origin, such as perhydrosqualene;

the hydrocarbon plant oils such as the liquid triglycerides of fatty acids having 4 to 10 carbon atoms, such as the triglycerides of heptanoic or octanoic acids, or else sunflower, corn, say, pumpkin, grapeseed, sesame, hazelnut, apricot, macadamia, castor and avocado oils, the triglycerides of caprylic/capric acids, such as those sold by the Stearineries Dubois Co. or those sold under the names Miglyol 810, 812 and 818 by Dynamit Nobel Co., jojoba oil and shea butter;

the straight or branched hydrocarbons of inorganic or synthetic origin, such as the paraffin oils and their derivatives, vaseline, the polydecenes, hydrogenated polyisobutene such as parleam; the isoparaffins, such as isohexadecane and isodecane;

the synthetic esters and ethers in particular from fatty acids such as the oils of formula $R_1COOR_2$, in which $R_1$ represents the residue of a higher fatty acid containing from 7 to 29 carbon atoms and $R_2$ represents a hydrocarbon chain containing from 3 to 30 carbon atoms, such as, for example, purcellin oil, isopropyl myristate, 2-ethylhexyl palmitate, 2-octyldodecyl stearate, 2-octyldodecyl erucate, isostearyl isostearate; the hydroxy esters such as isostearyl lactate, octyl hydroxystearate, octyldodecyl hydroxystearate, diisostearyl malate, triisocetyl citrate, heptanoates, octanoates, decanoates of fatty alcohols; polyol esters such as propylene glycol dioctanoate, neopentylglycol diheptanoate, diethylene glycol diisononanoate; and the esters of pentaerythritol;

fatty alcohols having 12 to 26 carbon atoms, particularly branched such as octyldodecanol, 2-butyloctanol, 2-hexyldecanol, 2-undecylpentadecanol;

the fluorinated oils with partly hydrocarbon and/or silicone structure such as those described in the document JP-A-2-295912, incorporated herein by reference;

the silicone oils such as the volatile or nonvolatile, straight or cyclic polymethylsiloxanes (PDMS), which are liquid or pasty at ambient temperature; the phenylsilicones such as the phenyltrimethicones, the diphenyldimethicones, the phenyldimethicones, the phenyltrimethylsiloxy diphenylsiloxanes;

the fluorinated oils and the fluorosilicone oils; and mixtures thereof.

The oily phase may represent from 0.1 to 30% and preferably from 10 to 25% of the total weight of the composition. These ranges include all specific values and subranges therebetween, such as 0.2, 0.5, 1, 2, 5, 8, 12, 15 and 20% by weight.

According to the invention, the composition can further comprise any additional ingredient customarily used in the fields of cosmetics and dermatology.

As an additional ingredient which can be used in the invention there can be cited the fillers, the preservatives, the antioxidants, the perfumes, the cosmetic or dermatological active principles and mixtures thereof. The quantities of these different ingredients are those generally used, for example in quantities ranging from 0.01 to 30% of the total weight of the composition. This range includes all specific values and subranges therebetween, such as 0.02, 0.05, 0.1, 0.2, 0.5, 1, 2, 5, 8, 10, 12, 15, 20 and 25% by weight. The nature of these ingredients and their proportions are compatible with obtaining the properties desired for the composition of the invention such as rheofluidizing, stability and viscoelasticity properties.

The term "fillers" refers to colorless or white, inorganic or synthetic, lamellar or nonlamellar particles. These fillers can be introduced into the composition for the purpose, in particular, of modifying the texture thereof. They can be present in proportions of 0 to 35%, preferably 0.5 to 15%, of the total weight of each composition. These ranges include all specific values and subranges therebetween, such as 0.01, 0.02, 0.05, 0.1, 0.2, 1, 2, 5, 10, 20, 25 and 30% by weight. Preferred examples include talc, zinc stearate, mica, kaolin, powders of nylon (especially Orgasol) and of polyethylene, Teflon, starch, boron nitride, microspheres of copolymers such as Expancel (Nobel Industrie), Polytrap (Dow Coming) and the microbeads of silicone resin (Tospearl of Toshiba, for example), or silica.

Depending on the presence or otherwise of coloring material and/or cosmetic or dermatological active principle, the composition of the invention may be prepared in the form of care cream for the skin, including the scalp, or for hair or nails, of sunscreen or skin-tanning agent, of makeup foundation, of lip product such as a gloss, of eye liner, mascara, concealer, body makeup product, shampoo and aftershampoo, or of cream for dermatological treatment of the skin, including the scalp.

The composition may be used by applying to the area desired to be treated. For example, a user may apply the composition to the skin and/or keratin fibers by spreading with the fingers. The composition may also be applied with an applicator device, such as a pad or a brush. Generally, the amount of composition to be applied is sufficient to coat the area to be treated to the desired thickness.

The compositions of the invention can be obtained according to well-known methods by mixing the hydrophilic ingredients in the aqueous phase and mixing the lipophilic ingredients in the oily phase, the associative polyurethane or polyurethanes and the surfactants being in particular mixed in with the aqueous phase, then by introduction of the oily phase into the aqueous phase and finally mixing so as to obtain a homogeneous product.

Having generally described this invention, a further understanding can be obtained by reference to certain specific examples which are provided herein for purposes of illustration only and are not intended to be limiting unless otherwise specified.

EXAMPLES

In the Examples below, the percentages refer % by weight in the composition.

Example 1

| Rheofluidizing Makeup Foundation | |
|---|---|
| Apricot kernel oil | 13% |
| Sicovit Yellow 10 E 172 | 0.8% |
| Sicomet Brown ZP 3569 | 0.67% |
| Sicovit Black 85 E 172 | 0.23% |
| Hombitan anatase FF Pharma | 5.3% |
| Propyl parahydroxybenzoate | 0.1% |
| Methyl parahydroxybenzoate | 0.2% |
| Triethanolamine, minimum 99% | 0.15% |
| Associative polyurethane (Ser-AD FX 1 100) | 2.24% |
| Cyclohexasiloxane (Dow-Corning 246 fluid) | 10% |
| Glycerin | 7% |
| Sterilized demineralized water    qsp | 100% |
| Polyethylene glycol stearate (PEG 8) | 1.3% |
| Stearic acid | 0.3% |
| Stearyl alcohol | 0.5% |
| Glucose stearate | 1.3% |

This formula has a viscosity which decreases with increasing shear rate, measured at 25° C. with a Rheomat 115: $2 \times 10^5$ cp at 0.3 rpm; $4 \times 10^4$ cp at 10 rpm; $5 \times 10^3$ cp at 100 rpm; $2 \times 10^2$ cp at $2 \times 10^3$ rpm.

When this formula is applied on the skin it forms a smooth, slightly satiny film. In addition, after the product has been taken from the jar with a finger (meaning manual shear), the surface of the product in the jar recovers its initial shape (closing up of the surface).

Example 2

| Rheofluidizing Care Cream | |
|---|---|
| Apricot kernel oil | 13% |
| Propyl parahydroxybenzoate | 0.1% |
| Methyl parahydroxybenzoate | 0.2% |
| Associative polyurethane (Ser-AD FX 1 100) | 2.24% |
| Cyclohexasiloxane (Dow-Corning 246 fluid) | 10% |
| Glycerin | 7% |
| Sterilized demineralized water    qsp | 100% |

This emulsion, without additional surfactant, has a viscosity, measured at 25° C. with a Rheomat 115 viscosimeter, of $5 \times 10^3$ cp at 10 rpm; $3 \times 10^3$ cp at 100 rpm; $2 \times 10^2$ cp at $2 \times 10^3$ rpm.

The foregoing compositions are prepared as follows: the fatty and aqueous phases are prepared separately and heated to around 70 to 80° C. The oily phase is introduced into the aqueous phase under agitation with a mechanical agitator of Moritz type. When the resulting emulsion begins to reach 40° C., the polyurethane gel prepared previously in water (concentration of the pregel 5%) is added progressively. Agitation is completed with a mechanical agitator of Rainery type.

Obviously, numerous modifications and variations of the present invention are possible in light of the above teachings. It is therefore to be understood that within the scope of the appended claims, the invention may be practiced otherwise than as specifically described herein.

This Application is based on French Patent Application Serial No. 98/08687, filed on Jul. 7, 1998, and incorporated herein by reference is its entirety.

What is claimed is:

1. A composition suitable for topical application to human skin, in the form of an oil-in-water emulsion, and comprising a liquid fatty phase, an aqueous phase, at least one coloring agent selected from the group consisting of fat-soluble coloring agents, water-soluble coloring agents, pigments, and mixtures thereof, and an associative polyurethane which is a nonionic copolymer containing a polyoxyethylenated hydrophilic sequence and a hydrophobic sequence of aliphatic and/or cycloaliphatic and/or aromatic chains, wherein the associative polyurethane is present in a thickening and leveling effective amount, and wherein said composition is otherwise substantially free of surfactants.

2. The composition of claim 1, wherein the associative polyurethane is present in at least 5 mg/m$^2$ of deployed surface of oil in water.

3. The composition of claim 1, wherein the associative polyurethane is present in of at least 10 mg/m$^2$ of deployed surface of oil in water.

4. The composition of claim 1, wherein the composition comprises 2 to 20% by weight of the associative polyurethane.

5. The composition of claim 1, wherein the composition comprises 3 to 10% by weight of the associative polyurethane.

6. The composition of claim 1, wherein the associative polyurethane is a block or graft polymer containing at least two alkyl chains of 6 to 30 carbon atoms, separated by a hydrophilic sequence.

7. The composition of claim 1, wherein the associative polyurethane is a three-block polymer.

8. The composition of claim 1, which has a viscosity of 1,000 to 10,000 cp (1 to 10 Pa.s), measured at 100 rpm at 25° C.

9. The composition of claim 1, comprising 0.1 to 30% by weight of the liquid fatty phase.

10. The composition of claim 1, comprising 10 to 25% by weight of the liquid fatty phase.

11. The composition of claim 1, wherein the liquid fatty phase comprises an oil or a mixture of oils selected from the group consisting of inorganic oils, plant oils, animal oils, synthetic oils, hydrocarbon oils, silicone oils, and fluorinated oils.

12. The composition of claim 11, wherein the oil or a mixture of oils has an Inorganic/Organic Balance of less than 0.42.

13. The composition of claim 1, comprising an amount of the associative polyurethane sufficient to emulsify the oil in the water.

14. The composition of claim 1, further comprising at least one member selected from the group consisting of preservatives, fillers, perfumes, cosmetic active agents, dermatological active agents, antioxidants, and mixtures thereof.

15. The composition of claim 1, which is in the form of a skin-care cream, a sunscreen or skin-tanning cream, a makeup foundation, a lip product, an eye liner, mascara, care cream for the hair or nails, a body makeup product, a shampoo, an after-shampoo, or a concealer.

16. A method of preparing the composition of claim 1, comprising combining the liquid fatty phase, the aqueous phase, and the associative polyurethane.

17. A method of thickening a composition, comprising incorporating a thickening and leveling effective amount of associative polyurethane into a composition comprising a liquid fatty phase, an aqueous phase, and at least one coloring agent selected from the group consisting of fat-soluble coloring agents, water-soluble coloring agents, pigments, and mixtures thereof, wherein the thickened composition is in the form of an oil-in-water emulsion and is suitable for topical application to human skin, and wherein said composition is otherwise substantially free of surfactants.

18. A method of treating skin, comprising applying the composition of claim 1 to the skin.

19. The method of claim 18, wherein the composition is applied to at least one type of skin selected from the group consisting of facial skin, body skin, and the lips.

20. A method of treating keratin fibers, comprising applying the composition of claim 1 to the keratin fibers.

21. The method of claim 20, wherein the composition is applied to at least one type of keratin fibers selected from the group consisting of eyelashes, eyebrows, and hair.

22. A composition suitable for topical application to human skin, in the form of an oil-in-water emulsion, and comprising a liquid fatty phase containing no surfactants and no oils having an Inorganic/Organic Balance of 0.42 or greater, an aqueous phase, at least one coloring agent selected from the group consisting of fat-soluble coloring agents, water-soluble coloring agents, pigments, and mixtures thereof, and an associative polyurethane which is a nonionic copolymer containing a polyoxyethylenated hydrophilic sequence and a hydrophobic sequence of aliphatic and/or cycloaliphatic and/or aromatic chains, wherein the associative polyurethane is present in a thickening and leveling effective amount, and wherein said composition is otherwise substantially free of surfactants.

23. A makeup foundation composition suitable for topical application to human skin, in the form of an oil-in-water emulsion, and comprising a liquid fatty phase, an aqueous phase, at least one coloring agent selected from the group consisting of fat-soluble coloring agents, water-soluble coloring agents, pigments, and mixtures thereof, and an associative polyurethane which is a nonionic copolymer containing a polyoxyethylenated hydrophilic sequence and a hydrophobic sequence of aliphatic and/or cycloaliphatic and/or aromatic chains, wherein the associative polyurethane is present in a thickening and leveling effective amount, and wherein said composition is otherwise substantially free of surfactants.

24. A makeup foundation composition suitable for topical application to human skin, in the form of an oil-in-water emulsion, and comprising a liquid fatty phase containing no surfactants and no oils having an Inorganic/Organic Balance of 0.42 or greater, an aqueous phase, at least one coloring agent selected from the group consisting of fat-soluble coloring agents, water-soluble coloring agents, pigments, and mixtures thereof, and an associative polyurethane which is a nonionic copolymer containing a polyoxyethylenated hydrophilic sequence and a hydrophobic sequence of aliphatic and/or cycloaliphatic and/or aromatic chains, wherein the associative polyurethane is present in a thickening and leveling effective amount, and wherein said composition is otherwise substantially free of surfactants.

25. A method of thickening a composition, comprising incorporating a thickening and leveling effective amount of associative polyurethane into a composition comprising a liquid fatty phase containing no surfactants and no oils having an Inorganic/Organic Balance of 0.42 or greater, an aqueous phase, and at least one coloring agent selected from the group consisting of fat-soluble coloring agents, water-soluble coloring agents, pigments, and mixtures thereof, wherein the thickened composition is in the form of an oil-in-water emulsion and is suitable for topical application to human skin, and wherein said composition is otherwise substantially free of surfactants.

* * * * *